United States Patent [19]

Moriizumi

[11] Patent Number: 5,325,858
[45] Date of Patent: Jul. 5, 1994

[54] ULTRASONIC IMAGING SYSTEM CAPABLE OF VARYING MAXIMUM PULSE REPETITION FREQUENCY DEPENDING UPON PULSE TRANSMISSION FREQUENCY

[75] Inventor: Takenori Moriizumi, Tochigiken, Japan

[73] Assignee: Kabushiki Kaisha Toshiba, Tokyo, Japan

[21] Appl. No.: 129

[22] Filed: Jan. 4, 1993

[30] Foreign Application Priority Data

Jan. 10, 1992 [JP] Japan .................................. 4-002785

[51] Int. Cl.$^5$ .............................................. A61B 8/00
[52] U.S. Cl. .................................. 128/660.07; 73/625
[58] Field of Search ...................... 128/660.01, 661.08, 128/661.09, 660.07, 660.09; 73/625, 626, 861.25; 367/105

[56] References Cited

U.S. PATENT DOCUMENTS

| | | | |
|---|---|---|---|
| 4,324,258 | 4/1982 | Huebscher et al. | 73/861.25 |
| 4,489,729 | 12/1984 | Sorenson et al. | 73/626 |
| 4,809,249 | 2/1989 | Barnes | 128/661.08 |
| 4,819,652 | 4/1989 | Micco | 128/661.09 |
| 4,852,577 | 8/1989 | Smith et al. | 73/625 |

Primary Examiner—William E. Kamm
Assistant Examiner—George Manuel
Attorney, Agent, or Firm—Oblon, Spivak, McClelland, Maier & Neustadt

[57] ABSTRACT

In an ultrasonic imaging system, a desirable ultrasonic image of an interior portion of a biological body scanned by ultrasonic pulses is obtained without occurrences of residual ultrasonic echoes and idle time. The ultrasonic imaging system includes an ultrasonic probe for transmitting ultrasonic pulses with a specific transmission frequency to a biological body under medical examination and for receiving ultrasonic echoes reflected from an interior portion of the biological body scanned by the ultrasonic pulses to derive an ultrasonic image signal; storage a unit for previously storing at least one PRF (pulse repetition frequency) value fixed only corresponding to the transmission frequency of the ultrasonic pulses transmitted from the ultrasonic probe; and a control unit for reading the PRF value from the storage unit when the specific transmission frequency is set, and for controlling the ultrasonic probe in such a manner that the ultrasonic pulses with the transmission frequency are transmitted and the ultrasonic echoes are received by the ultrasonic probe within a time period determined by the PRF value, thereby producing an ultrasonic image of the scanned interior portion by processing the ultrasonic image signal.

12 Claims, 10 Drawing Sheets

ULTRASONIC IMAGING SYSTEM CAPABLE OF VARYING MAXIMUM PULSE REPETITION FREQUENCY DEPENDING UPON PULSE TRANSMISSION FREQUENCY

BACKGROUND OF THE INVENTION

1. Field of the Invention

The present invention generally relates to an ultrasonic imaging system for transmitting ultrasonic pulses with a transmission frequency in accordance with a pulse repetition frequency (PRF) to a biological body under medical examination, and for receiving ultrasonic echoes reflected from the scanned interior of the biological body to obtain an ultrasonic image of this interior. More specifically, the present invention is directed to such an ultrasonic imaging system capable of varying a maximum pulse repetition frequency based upon various conditions such as ultrasonic pulse transmission frequencies and field depths.

2. Description of the Prior Art

Figure 1:
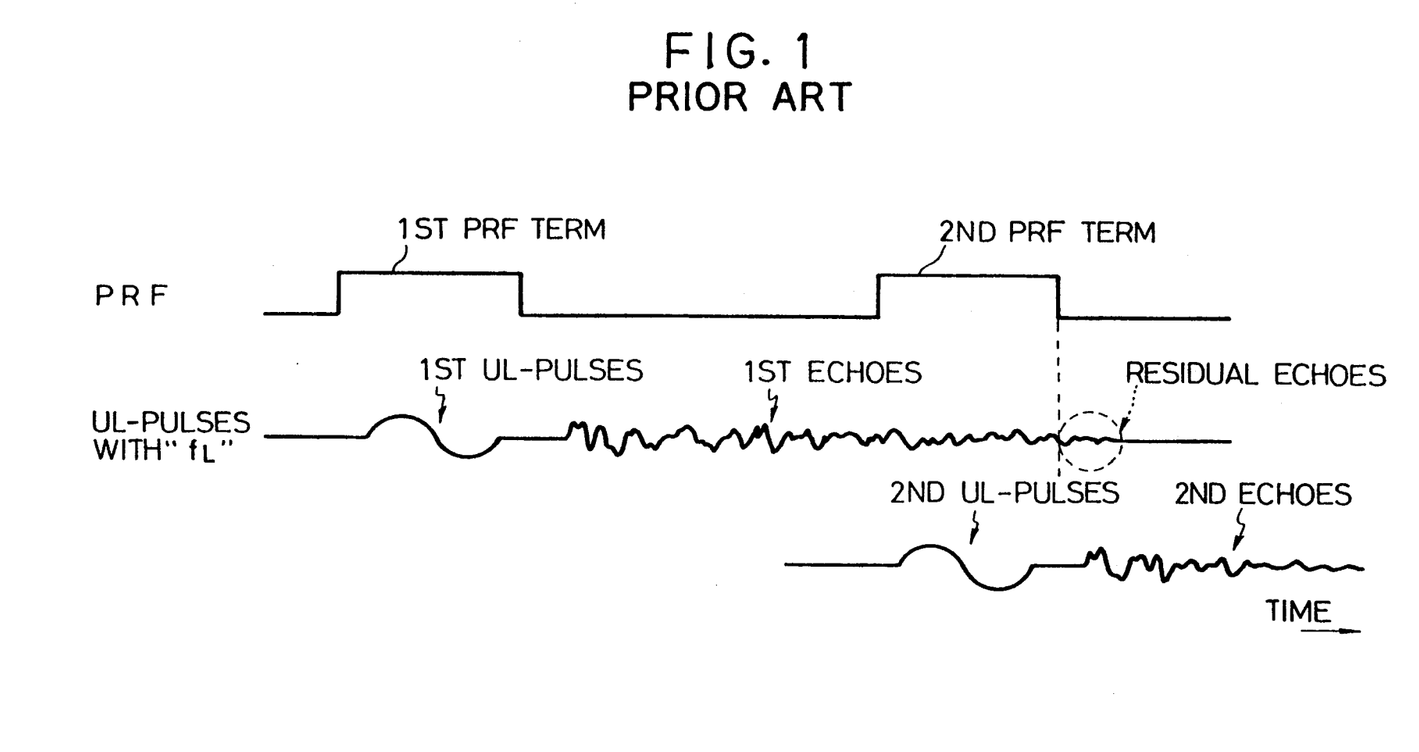
FIG. 1 schematically represents an occurrence of residual echoes in the conventional ultrasonic imaging system.

In general, when ultrasonic pulses are transmitted from an ultrasonic probe of a conventional ultrasonic imaging system to a biological body under medical examination, and ultrasonic echoes reflected from the scanned interior of the biological body are received by this ultrasonic probe to image a sectional view of tissues within this interior, if a pulse repetition frequency (PRF) is preset to a high frequency with respect to the transmission frequency "$f_L$" of the ultrasonic pulses, residual echoes happen to occur in the received echoes. Then, the residual echoes may cause qualities of the ultrasonic images to be deteriorated. An occurrence of such a residual echo will now be described more in detail. That is, as represented in FIG. 1, during a first PRF term, first ultrasonic (UL) pulses are transmitted and also first echoes are received. However, since the first echoes are still present even when a second PRF term is commenced (namely, second ultrasonic pulses are being transmitted), the rear portions of these first echoes are mixed with the front portions of the second echoes, which produces so-called "residual echoes". Accordingly, in order not to produce or receive such residual echoes, the upper limit value of this pulse repetition frequency (PRF) is preset. This upper limit value is fixed for each of the conventional ultrasonic imaging systems. Accordingly, the ultrasonic pulses and the ultrasonic echoes are transmitted/received in accordance with a PRF value lower than this fixed upper limit value in the conventional ultrasonic imaging system.

Figure 2:
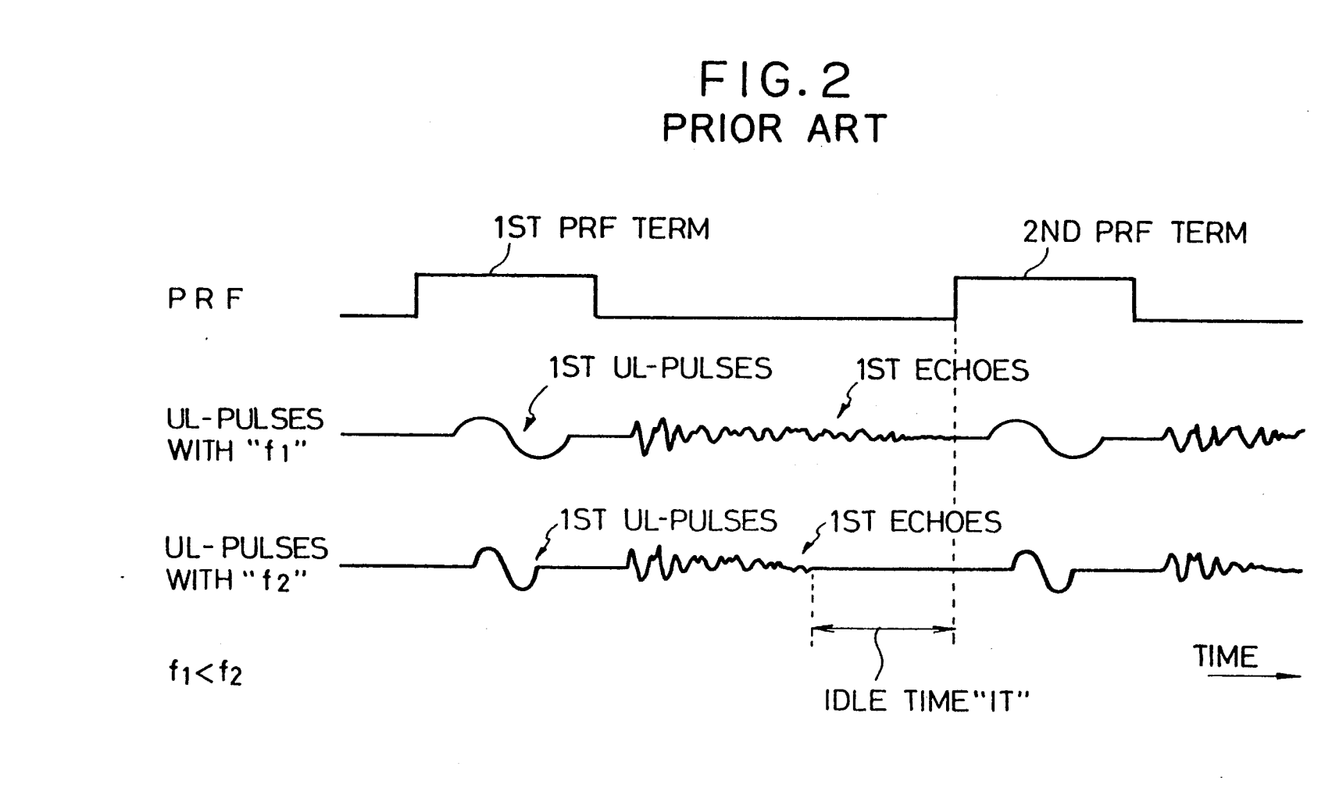
FIG. 2 schematically illustrates an occurrence of idle time "IT" in the conventional ultrasonic imaging system.

However, the above-described conventional ultrasonic imaging system has the following drawbacks. That is, generally speaking, an occurrence of such residual echoes depends upon a transmission frequency ($f_L$) of ultrasonic pulses, and several sorts of ultrasonic probes having different transmission frequencies such as 3.5 MHz, 5 MHz and 7 MHz are utilized within a single ultrasonic imaging system. However, as previously explained, since the upper limit value of the pulse repetition frequency has been preselected to one fixed value (constant PRF value) even when these different transmission frequencies are utilized in a single ultrasonic imaging system, the reception time period within the PRF term is not always effectively utilized. This second problem will now be explained more in detail with reference to FIG. 2. In FIG. 2, it is assumed that a first ultrasonic probe with a first transmission frequency "$f_1$" is employed at a first examination stage under the fixed PRF value. In this case, for instance, since the first echoes can be completely received within the first PRF term, neither the above-mentioned residual echoes, nor idle time "IT" is produced. Thereafter, a second ultrasonic probe with a second transmission frequency "$f_2$" is employed to replace the first ultrasonic probe with the first transmission frequency "$f_1$". It should be noted that the second transmission frequency "$f_2$" is higher than that first transmission frequency "$f_1$". As apparent from FIG. 2, the first echoes produced under the second transmission frequency "$f_2$" are attenuated within a short time period, as compared with the first echoes produced under the first transmission frequency "$f_1$". As a consequence, an idle time "IT" is produced before the subsequent second ultrasonic pulses are transmitted from the second ultrasonic probe with the second transmission frequency "$f_2$".

SUMMARY OF THE INVENTION

The present invention has been made in an attempt to solve the above-described problems of the conventional ultrasonic imaging systems, and therefore, has, as an object, to provide an ultrasonic imaging system capable of effectively utilizing an echo reception time period within a PRF term without any residual echoes.

Another object of the present invention is to provide an ultrasonic imaging system capable of improving a quality of an ultrasonic image, while utilizing plural ultrasonic probes with various different transmission frequencies.

To achieve the above-described objects and other features, an ultrasonic imaging system, according to one aspect of the present invention, comprises:

ultrasonic probe means (5) for transmitting ultrasonic pulses with a specific transmission frequency ($f_A, f_B$) to a biological body under medical examination and for receiving ultrasonic echoes reflected from an interior portion of the biological body scanned by the ultrasonic pulses to derive an ultrasonic image signal;

storage means (104) for previously storing at least one PRF (pulse repetition frequency) value fixed only to the specific transmission frequency of the ultrasonic pulses transmitted from the ultrasonic probe means (5);

control means (102,106) for reading said PRF value from the storage means (104) when said transmission frequency ($f_A, f_B$) is set and for controlling said ultrasonic probe means (5) in such a manner that said ultrasonic pulses with said transmission frequency ($f_A, f_B$) are transmitted and said ultrasonic echoes are received by said ultrasonic probe means (5) within a time period determined by said PRF value, thereby producing an ultrasonic image of said scanned interior portion by processing said ultrasonic image signal.

Furthermore, according to another aspect of the present invention, an ultrasonic imaging system comprises:

ultrasonic probe means (5) for transmitting ultrasonic pulses with a specific transmission frequency ($f_A, f_B$) to a biological body under medical examination and for receiving ultrasonic echoes reflected from an interior portion of the biological body scanned by the ultrasonic pulses to derive an ultrasonic image signal;

field-depth setting means (60) for setting a field depth of an ultrasonic pulse scanning operation;

storage means (204) for previously storing at least one PRF (pulse repetition frequency) value fixed to both of said specific transmission frequency ($f_A, f_B$) of the ultrasonic pulses and said field depth of the ultrasonic pulse scanning operation;

control means (202) for reading said PRF value from said storage means (204) when said transmission frequency ($f_A, f_B$) and said field depth are set, and for controlling said ultrasonic probe means (5) in such a manner that said ultrasonic pulses with said transmission frequency ($f_A, f_B$) are transmitted and said ultrasonic echoes are received by said ultrasonic probe means (5) within a time period determined by both of said PRF value and said field depth, thereby producing an ultrasonic image of said scanned interior portion by processing said ultrasonic image signal.

Moreover, according to another aspect of the present invention, an ultrasonic imaging system comprises:

ultrasonic probe means (5) for transmitting ultrasonic pulses with a specific transmission frequency ($f_A, f_B$) to a biological body under medical examination and for receiving ultrasonic echoes reflected from an interior portion of the biological body scanned by the ultrasonic pulses to derive an ultrasonic image signal;

field-depth setting means (62) for setting a field depth of an ultrasonic pulse scanning operation;

storage means (804) for previously storing at least one maximum PRF (pulse repetition frequency) value fixed only to said specific transmission frequency ($f_A, f_B$) of the ultrasonic pulses transmitted from the ultrasonic probe means (5);

calculation means (306) for calculating an actual PRF value by using said set field depth based upon a PRF calculating formula;

comparator means (808) for comparing said actual PRF value calculated in said calculation means (306) with said maximum PRF value read out from said storage mean (304) to determine a PRF value suitable for said ultrasonic pulse scanning operation; and control means (302) for controlling said ultrasonic probe means (5) in such a manner that said ultrasonic pulses with said transmission frequency ($f_A, f_B$) are transmitted and said ultrasonic echoes are received by said ultrasonic probe means (5) within a time period determined by said suitable PRF value, thereby producing an ultrasonic image of said scanned interior portion by processing said ultrasonic image signal.

BRIEF DESCRIPTION OF THE DRAWINGS

For a better understanding of the present invention, reference is made of the following detailed description in conjunction with the accompanying drawings, in which.

DETAILED DESCRIPTION OF THE PREFERRED EMBODIMENTS

Basic Ideas

Before proceeding with descriptions of various preferred embodiments, basic ideas of the ultrasonic imaging system according to the present invention will now be summarized.

In accordance with a first basic idea of the present invention, an upper limit value of a pulse repetition frequency (PRF) is variable, depending upon specific transmission frequencies of ultrasonic pulses transmitted from ultrasonic probes. In other words, a plurality of PRF values (fixed upper limit values) which have been determined based upon only the transmission frequencies of the ultrasonic pulses, are previously stored in a central processing unit (CPU) of an ultrasonic imaging system (see FIG. 3). That is to say, for instance, when three sorts of ultrasonic probes having three transmission frequencies different from each other are employed in a single ultrasonic imaging system, three different PRF upper limit values are determined for three different transmission frequencies in one-to-one correspondence.

Then, in accordance with a second basic idea, a plurality of PRF values (fixed upper limit values) are determined based on both of the specific transmission frequencies and the field depths of the ultrasonic pulses. These PRF values are previously stored in the CPU as a memory table, for example.

According to a third basic idea of the present invention, a proper PRF upper limit value is calculated based on both of this specific transmission frequency and also a field depth of the ultrasonic pulse in accordance with a preselected algorithm.

Overall Circuit Arrangement of First Ultrasonic Imaging System

Figure 3:
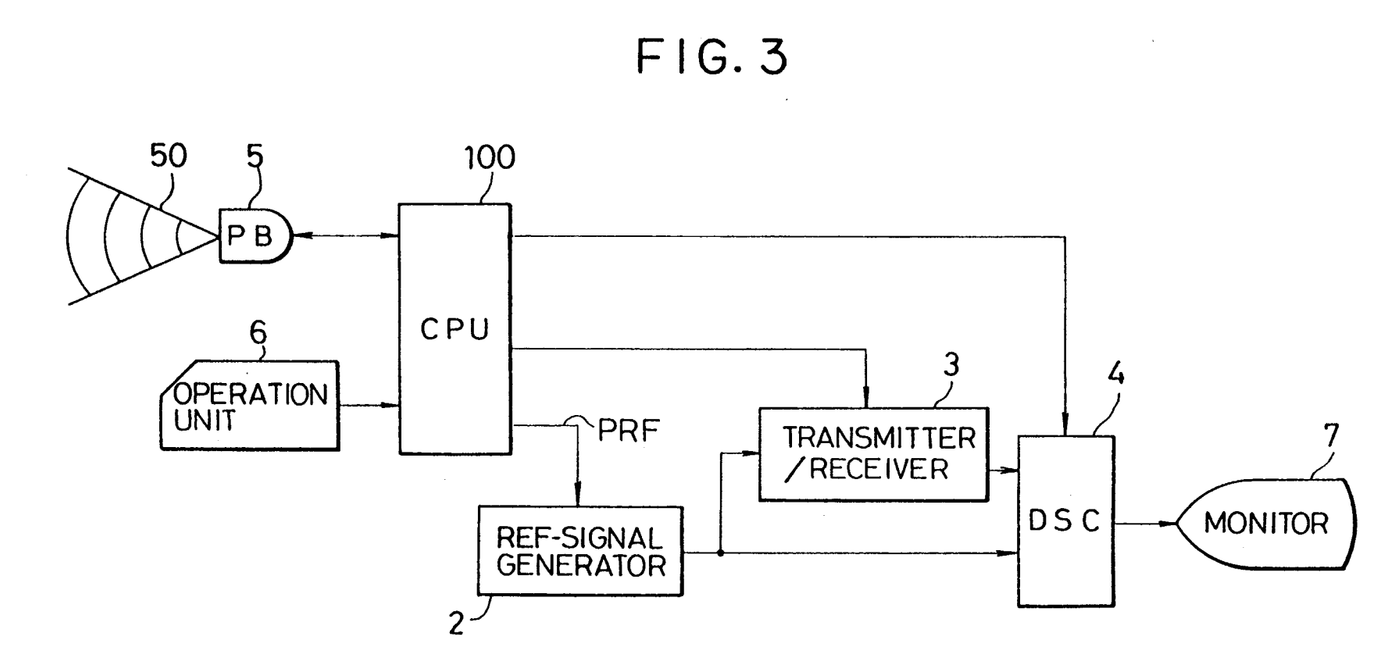
FIG. 3 is a schematic block diagram for showing an overall circuit arrangement of an ultrasonic imaging system according to a first preferred embodiment of the present invention.

Referring now to FIG. 3, an overall circuit arrangement of an ultrasonic imaging system according to a first preferred embodiment of the present invention will be described, which is accomplished based upon the above-described first basic idea.

In the first ultrasonic imaging system shown in FIG. 3, a central processing unit 100 functions as a major featured circuit element of this first imaging system (will be discussed later in detail), and also a system control unit thereof. The first ultrasonic imaging system further includes a reference signal generating unit 2, a transmitter/receiver unit 3, a digital scan converter 4, an ultrasonic probe 5, an operation unit 6, and a TV monitor 7. Under control of the CPU 100, the reference signal generating unit 2 generates reference signals used to control timings of ultrasonic pulse transmission and also ultrasonic echo reception.

Various operation data are inputted from the operation unit 6 via the CPU 100 to the relevant circuits employed in the first ultrasonic imaging system. From the ultrasonic probe 5, the ultrasonic pulses 50 having the specific transmission frequency of, e.g., 5 MHz are transmitted to scan a biological body under medical examination (not shown in detail) in accordance with a predetermined PRF (pulse repetition frequency) timing in response to a probe energizing signal from the transmitter/receiver unit 3. Ultrasonic echoes are reflected from the interior of this biological body scanned by the ultrasonic pulses and then received by the same ultrasonic probe 5 to be converted into ultrasonic echo signals. The ultrasonic echo signals are supplied via the transmitter/receiver unit 3 to the digital scan converter 4, and then are converted into a desirable ultrasonic imaging signal related to the scanned interior of the biological body under control of the CPU 100.

As a result, a desirable ultrasonic image related to the scanned interior (e.g., tissues and organs) within the biological body under medical examination.

Internal Arrangement of CPU 100

Figure 4:
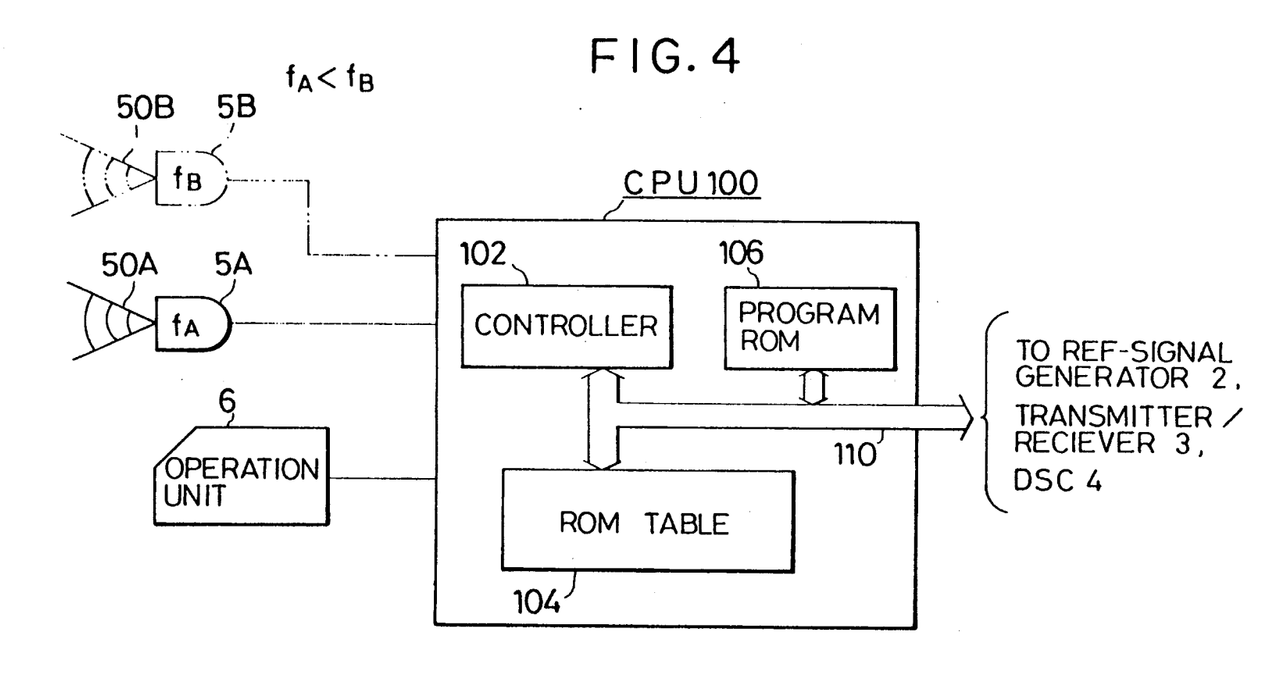
FIG. 4 schematically shows an internal circuit arrangement of the major circuit in the first ultrasonic imaging system.

FIG. 4 schematically represents an internal arrangement of the CPU 100 employed in the first ultrasonic imaging system shown in FIG. 3.

This CPU 100 is mainly constructed of a controller 102, a ROM (read-only memory) table 104 and a system program ROM 106, which are mutually coupled via a bus 110 to each other.

In the ROM table 104, there is prepared a conversion table for previously storing data about a plurality of PRF values. According to the first basic idea of the present invention, as previously explained, these PRF values correspond only to the specific transmission frequencies of the ultrasonic pulses 50. In an example of FIG. 4, two different transmission frequencies "$f_A$" and "$f_B$" specific to two ultrasonic probes 5A and 5B are employed with such a relationship: $f_A < f_B$. Assuming now that the first transmission frequency "$f_A$" of the ultrasonic pulses 50A transmitted from the first ultrasonic probe 5A is selected to the 5 MHz, a first PRF value becomes, e.g., 3.7 KHz. Also, if it is assumed that the second transmission frequency "$f_B$" of the ultrasonic pulses 50B transmitted from the second ultrasonic probe 5B is selected to 7.5 MHz, a second PRF value becomes 4.5 KHz. Then, this ROM table 104 previously stores therein the first PRF value (3.7 KHz) and the second PRF value (4.5 KHz).

It should be noted that these first and second PRF values are selected in such manner that neither residual echoes are produced, nor idle time "IT" is produced.

Detailed Operation of First Ultrasonic Imaging System

Referring now to a flow chart shown in FIG. 5, operations of the first ultrasonic imaging system will be described more in detail.

At a first step ST-1 of the flow chart, the first ultrasonic probe 5A is mounted to the first ultrasonic imaging system indicated in FIG. 3. Then, the mounted first ultrasonic probe 5A is designated by operating the operation panel 6 at a step ST-2, so that the first transmission frequency "$f_A$ (5 MHz)" of the ultrasonic pulses is designated into the CPU 100. At the next step ST-4, in response to the designated data supplied from the operation unit 6, data about the first PRF value, or upper limit value (3.7 KHz) is read out from the ROM table 104 under control of the controller 102. Thus, the first PRF value data is supplied to the reference signal generating unit 2 (see FIG. 3) via the bus 110. Furthermore, other control data are supplied via this bus 110 to the transmitter/receiver unit 3 and the digital scan converter 4 under control of the controller 102 in accordance with the system program stored in the program ROM 106 at a step ST-5.

As a result, the first probe 5A and the relevant circuits are driven under the above-described conditions at a step ST-8. Thus, the the reflection pulses are acquired by the first ultrasonic probe 5A and the transmitter/receiver unit 3, and then the ultrasonic image signals are produced from the digital scan converter 4, so that the desirable ultrasonic image of the scanned interior within the biological body with the better image quality can be displayed on the TV monitor 7 at a step ST-9 under control of the controller 102.

After the first ultrasonic probe 5A and the relevant circuits have been driven, the process operation may be returned to the first step ST-1 at which the second ultrasonic probe 5B may be mounted instead of the first ultrasonic probe 5A. Then, the second transmission frequency "$f_B$ (7.5 MHz)" of the second ultrasonic probe 5B is designated by the operation unit 6 at the step ST-2.

Similarly, the second PRF value (4.5 KHz) data is read out from the ROM table 104 which will then be supplied to the reference signal generating unit 2. As a consequence, the second ultrasonic probe 5B is driven and another desirable ultrasonic image of the scanned interior of the biological body is displayed on the TV monitor 7.

Figure 5:
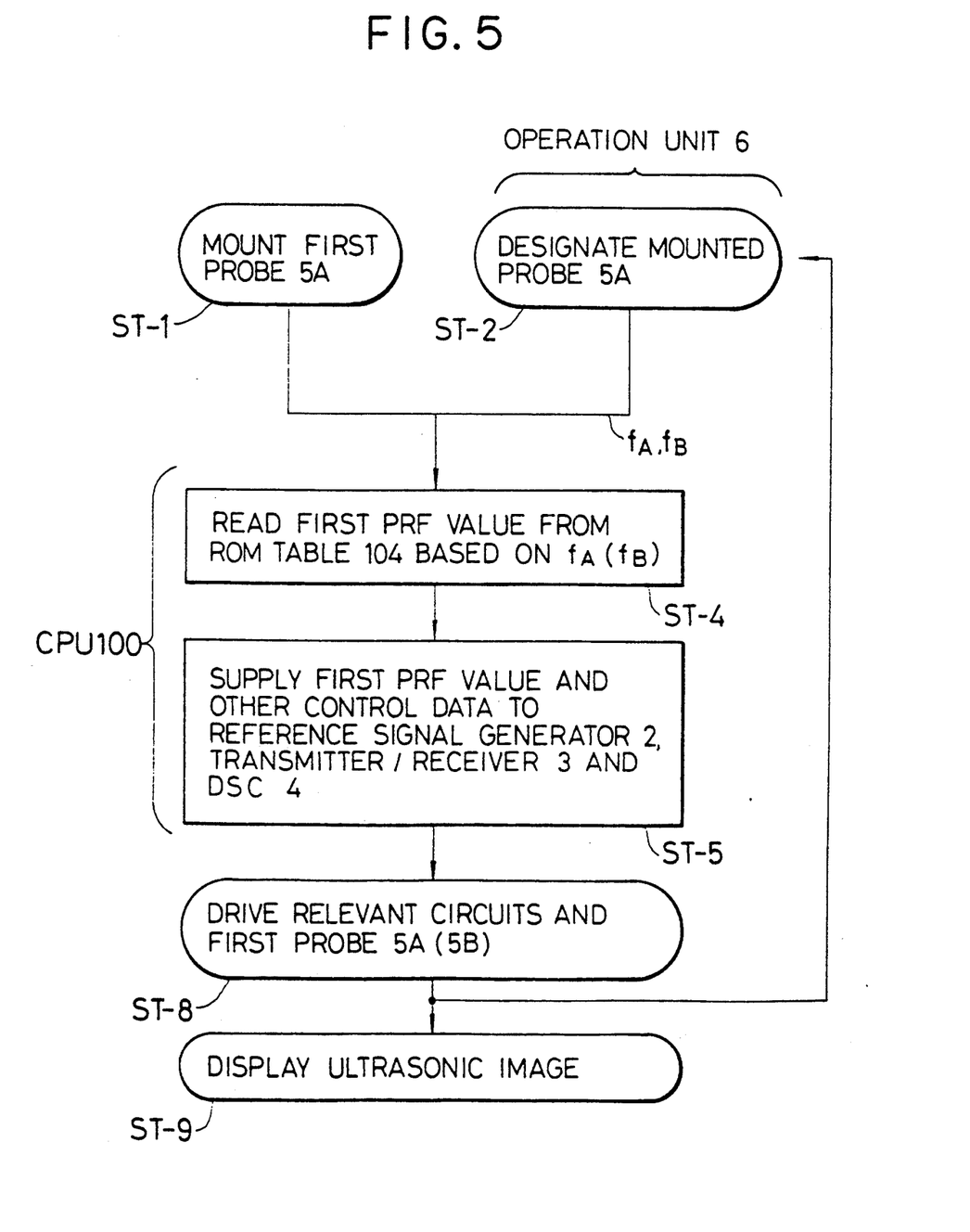
FIG. 5 is a flow chart for explaining operations of the first ultrasonic imaging system.

As previously explained, in accordance with the first ultrasonic imaging system represented in FIGS. 3 to 5, the PRF values may be varied, depending upon only the specific transmission frequencies "$f_A$", "$f_B$" of the ultrasonic probes 5A, 5B, within such a range where neither residual echoes happen to occur, nor idle time "IT" (see FIG. 2) is produced even if the high transmission frequency "$f_B$" is selected. Moreover, since the high transmission frequency of the ultrasonic pulses can be utilized without any difficulties, a rapid-moving organ such as a heart can be precisely ultrasonic-imaged. Also, even when the field depth is changed, a constant number of ultrasonic image frame can be maintained.

Arrangement of Second Ultrasonic Imaging System

Figure 6:
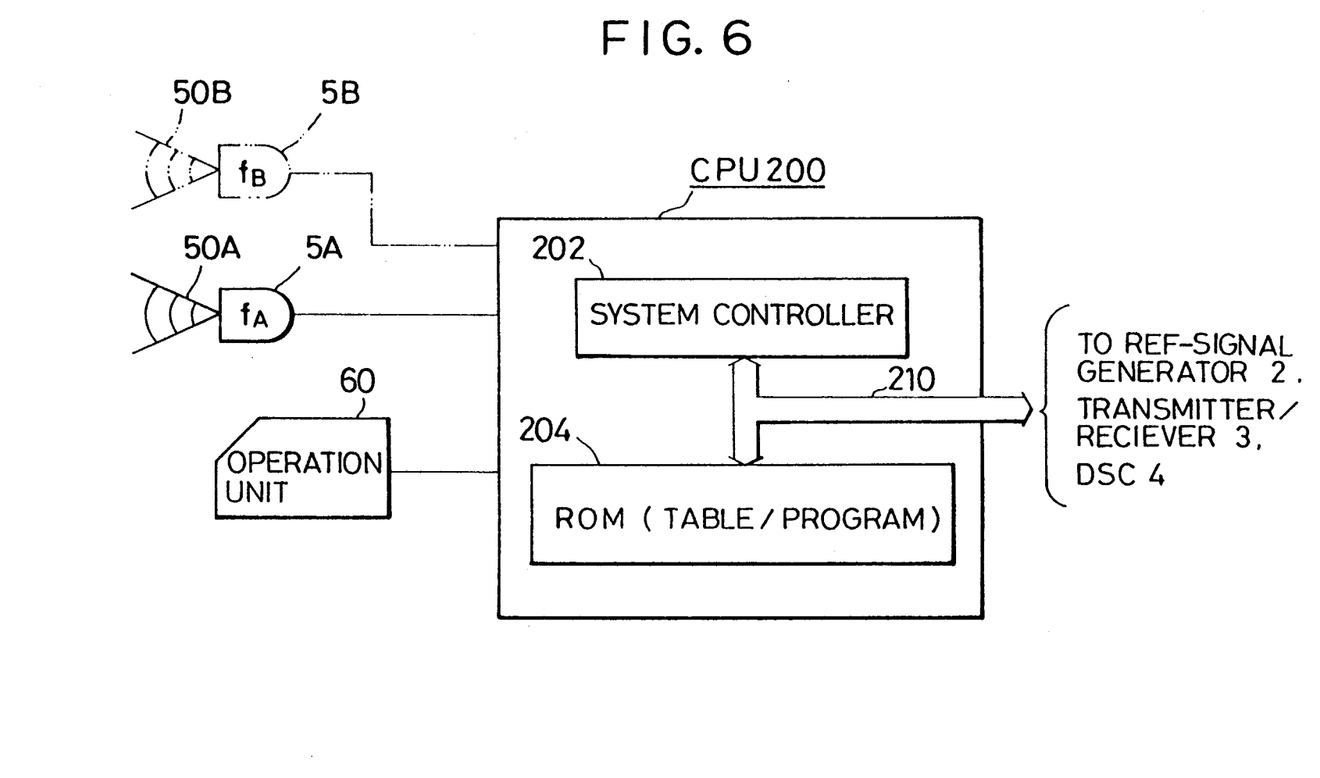
FIG. 6 schematically represents an internal circuit arrangement of a major circuit in an ultrasonic imaging system according to a second preferred embodiment of the invention.

FIG. 6 schematically represents a major circuit arrangement of an ultrasonic imaging system according to a second preferred embodiment of the present invention, which is accomplished based upon the second basic idea. It should be noted that since other circuit arrangements are similar to those of the first ultrasonic imaging system shown in FIG. 3, only an internal circuit arrangement of a CPU 200 and the relevant circuits 5A, 5B and 6 are shown in FIG. 6. In other words, the CPU 100 of the first ultrasonic imaging system shown in FIG. 3 is substituted by this CPU 200 shown in FIG. 6 so as to constitute the entire arrangement of the second ultrasonic imaging system. Accordingly, only different circuit arrangements and operations thereof will now be described.

As apparent from FIG. 6, this CPU 200 is mainly constructed of a system controller 202 and a ROM 204 having a conversion table (not shown in detail) and previously storing a system program. The system controller 202 is mutually connected to the ROM 204 via a bus 210. Also, this CPU 200 is coupled via the bus 210 to the reference signal generating unit 2, the transmitter/receiver unit 3, and the digital scan converter 4.

Operation of Second Ultrasonic Imaging System

Figure 7:
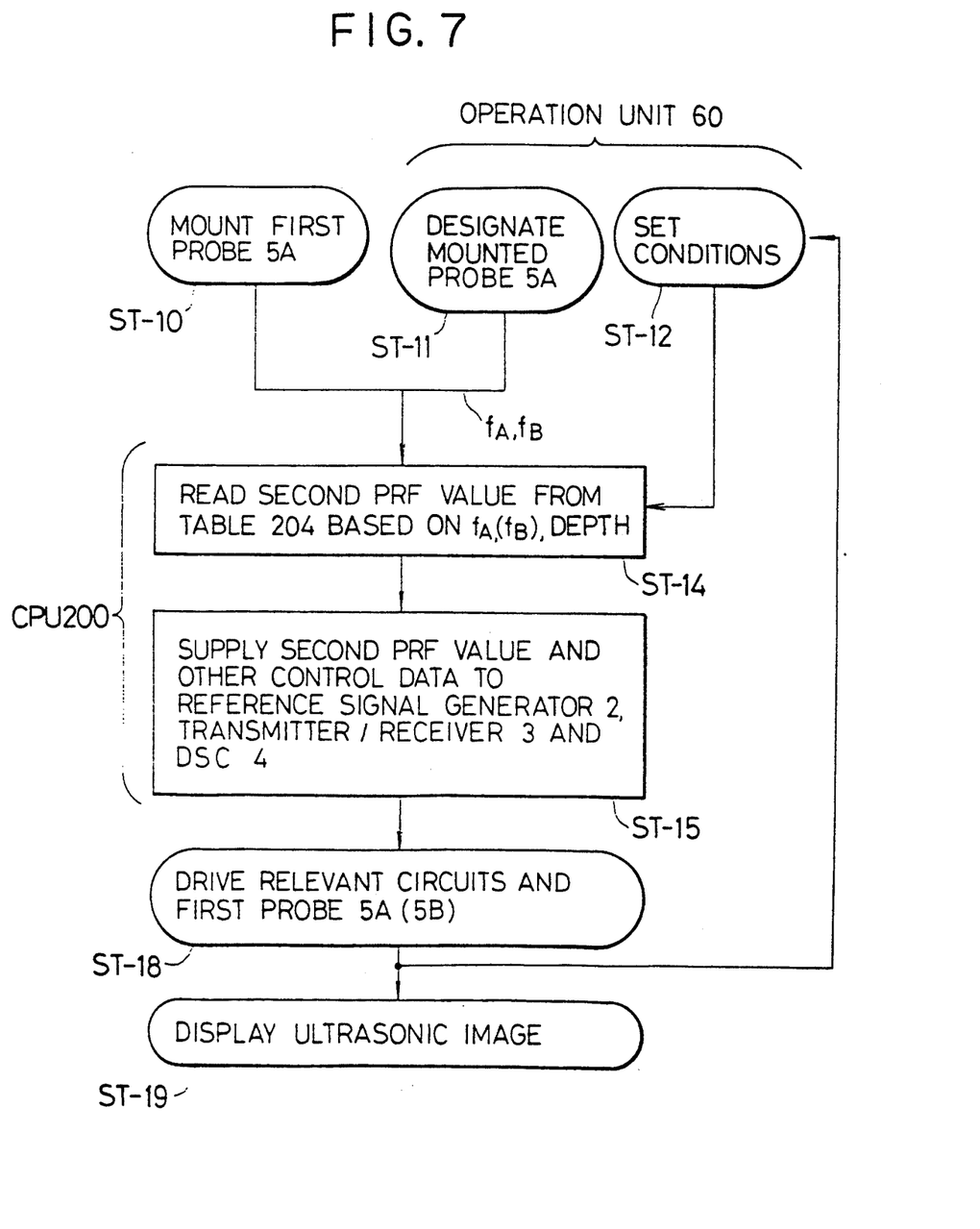
FIG. 7 is a flow chart for explaining operations of the second ultrasonic imaging system.

Operations of the second ultrasonic imaging system accomplished by the second basic idea of the present invention will now be explained with reference to a flow chart of FIG. 7 and waveform charts of FIGS. 8A and 8B.

At a first step ST-10, the first ultrasonic probe 5A is mounted on the second ultrasonic imaging system. Thereafter, the mounted probe 5A is designated by manipulating the operation unit 60 to set the first transmission frequency "$f_A$(5 MHz)" at a step ST-11 and also ultrasonic imaging conditions, e.g., field depth are set by operating the operation unit 60 at a step ST-12.

Then, at a step ST-14, the data about the first PRF value (3.7 KHz) corresponding to this first transmission frequency "$f_A$" and the set field depth is read out from the conversion table of the ROM 204 under control of the system controller 202. The read first PRF value data is supplied via the bus 210 to the reference signal generating unit 2 so as to generate a first PRF control signal later (see FIG. 8A) at a step ST-15.

Figure 8A:
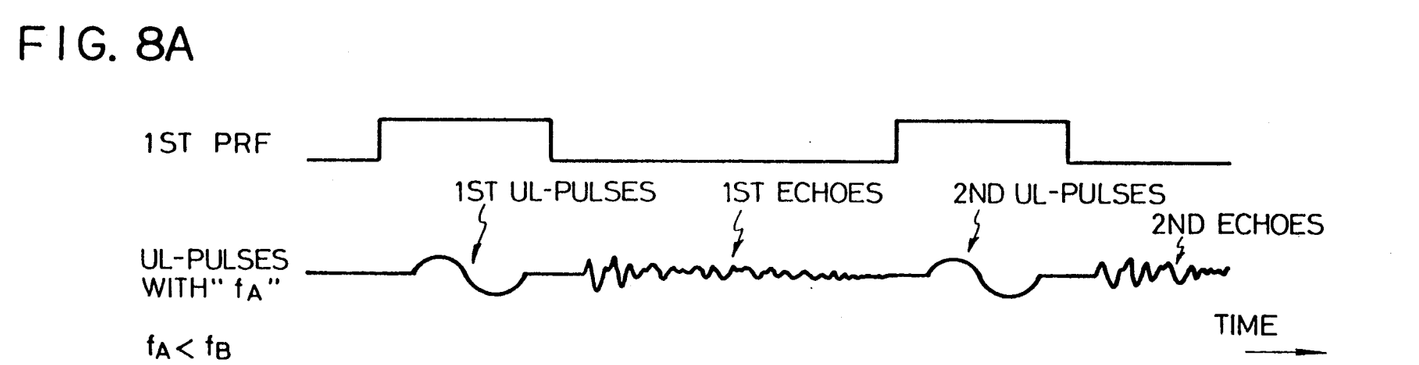
FIGS. 8A and 8B are waveform charts of the ultrasonic pulses and echoes appearing in the second ultrasonic imaging system.
Figure 8B:
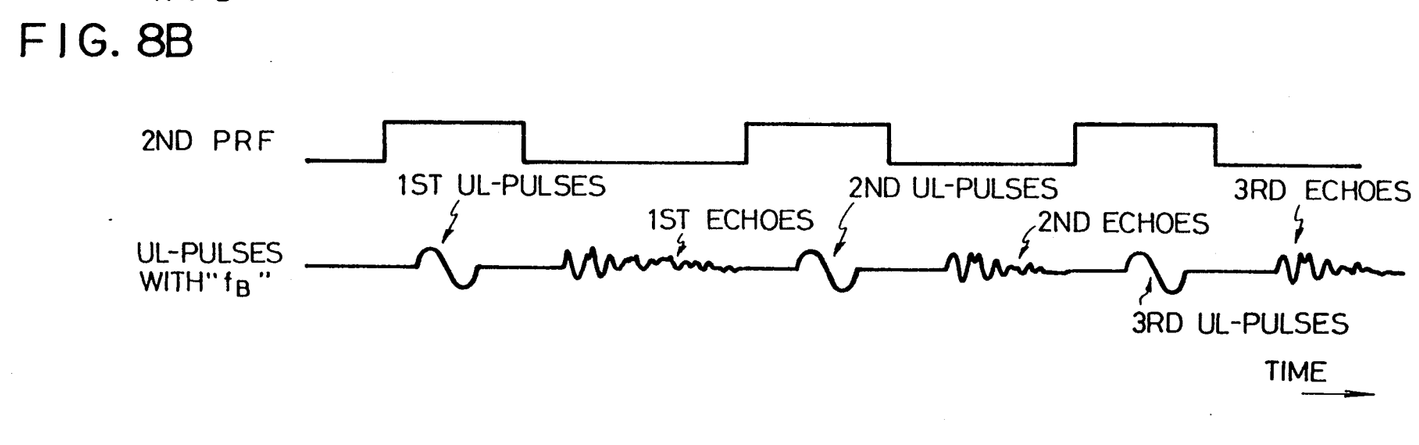

At the subsequent step ST-18, the first ultrasonic probe 5A is driven by the transmitter/receiver unit 3 to acquire echo signals in accordance with the first PRF specific signal as shown in FIG. 8A. As apparent from FIG. 8A, since the respective echoes can be completely received within the respective first PRF terms (namely, time period defined by first PRF value), neither residual echoes nor idle time "IT" (see FIG. 2) appears in the received echoes. Accordingly, a desirable ultrasonic image of the scanned interior of the biological body can be displayed on the TV monitor 7 with maintaining an image quality at satisfactory levels at a step ST-19.

Subsequently, the first ultrasonic probe 5A with the first specific transmission frequency "$f_A$" is substituted by the second ultrasonic probe 5B with the second specific transmission frequency "$f_B$" at the step ST-10. Then, the mounted second ultrasonic probe 5B is designated by the operation unit 60 to input the data about the second transmission frequency "$f_B$(7.5 MHz)" at the step ST-11. Furthermore, the depth condition of this second ultrasonic probe 5B is similarly set at the step ST-12 by the operation unit 60.

Under such a circumstance, the data about the second PRF value (4.5 KHz) corresponding to both of the second transmission frequency "$f_B$" and the set depth is derived from the conversion table of the ROM 204 at the step ST-14. This second PRF value data is supplied to the reference signal generating unit 2 (see FIG. 3) at the step ST-15.

Next, the second ultrasonic probe 5B is driven to acquire ultrasonic echoes reflected from the scanned interior of the biological body in accordance with the second PRF signal under control of the system controller 202 at the step ST-18. These second ultrasonic pulses, second ultrasonic echoes and second PRF signal are shown in FIG. 8B. As apparent from FIG. 8B, each of these ultrasonic echoes can be completely received within the respective PRF terms without occurrences of residual echoes as well as idle times.

As a consequence, a desirable ultrasonic image of the interior scanned by the second ultrasonic images 5B can be displayed on the TV monitor 7 at the step ST-19 with maintaining better image qualities, because neither residual echoes (see FIG. 1), nor idle time (see FIG. 2) happens to occur.

Arrangement of Third Ultrasonic Imaging System

Figure 9:
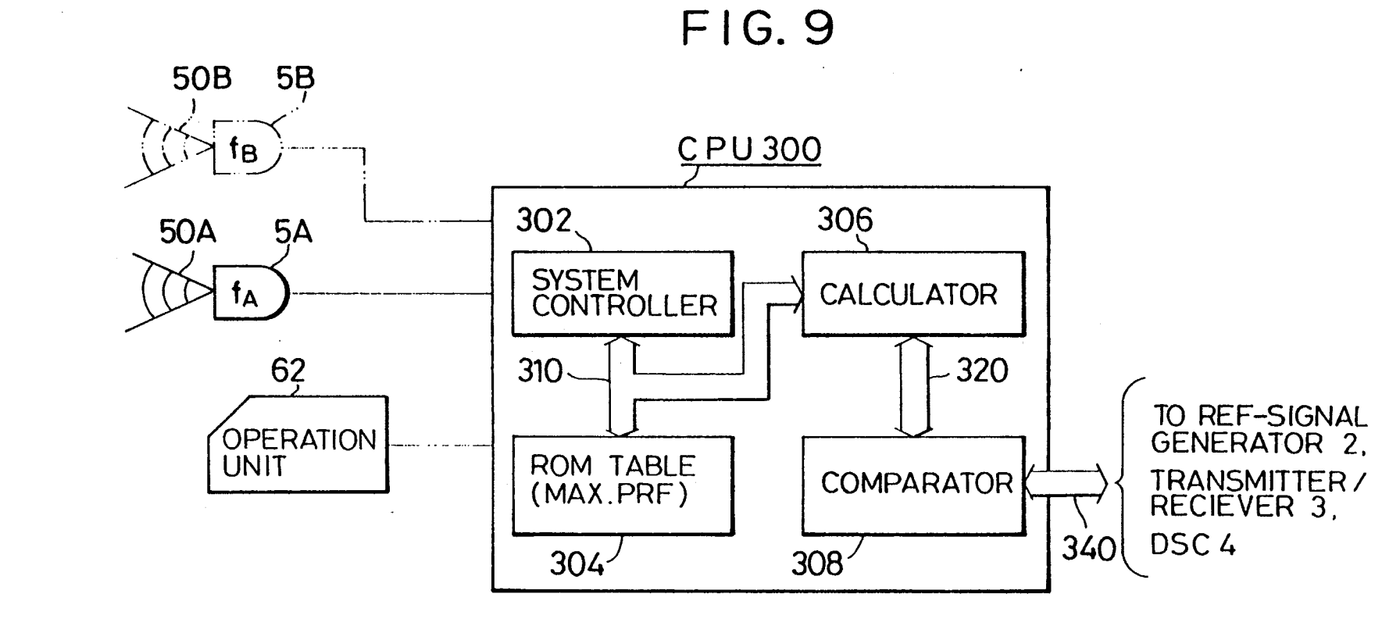
FIG. 9 is a schematic block diagram of an internal circuit arrangement of a major circuit employed in another ultrasonic imaging system according to a third preferred embodiment of the present invention.

FIG. 9 schematically shows a major circuit arrangement of another ultrasonic imaging system according to a third preferred embodiment of the present invention, which is accomplished based on the above-explained third basic idea of this invention.

Similar to the second ultrasonic imaging system of FIG. 6, this major circuit of FIG. 9 is mainly constructed of a central processing unit 300 and an operation unit 62. Since remaining circuit arrangement of the third ultrasonic imaging system is similar to that of the first ultrasonic imaging system shown in FIG. 3, no further explanation thereof is made in the following description.

As seen from FIG. 9, the CPU 300 includes a system controller 302, a ROM table 304, a calculator 306 and a comparator 308. These circuit elements are mutually connected to each other via buses 310 and 320. The ROM table 304 previously stores maximum (upper limit) PRF values preset for the specific transmission frequencies "$f_A$", "$f_B$" of the ultrasonic pulses emitted from the first and second ultrasonic probes 5A, 5B. The calculator 306 calculates an actual PRF value based upon a field depth set by the operation unit 62 in accordance with a predetermined PRF calculating formula. The comparator 308 compares the calculated actual PRF value with the corresponding maximum PRF value read out from the ROM table 304 to determine a suitable PRF value.

Operation of Third Ultrasonic Imaging System

Figure 10:
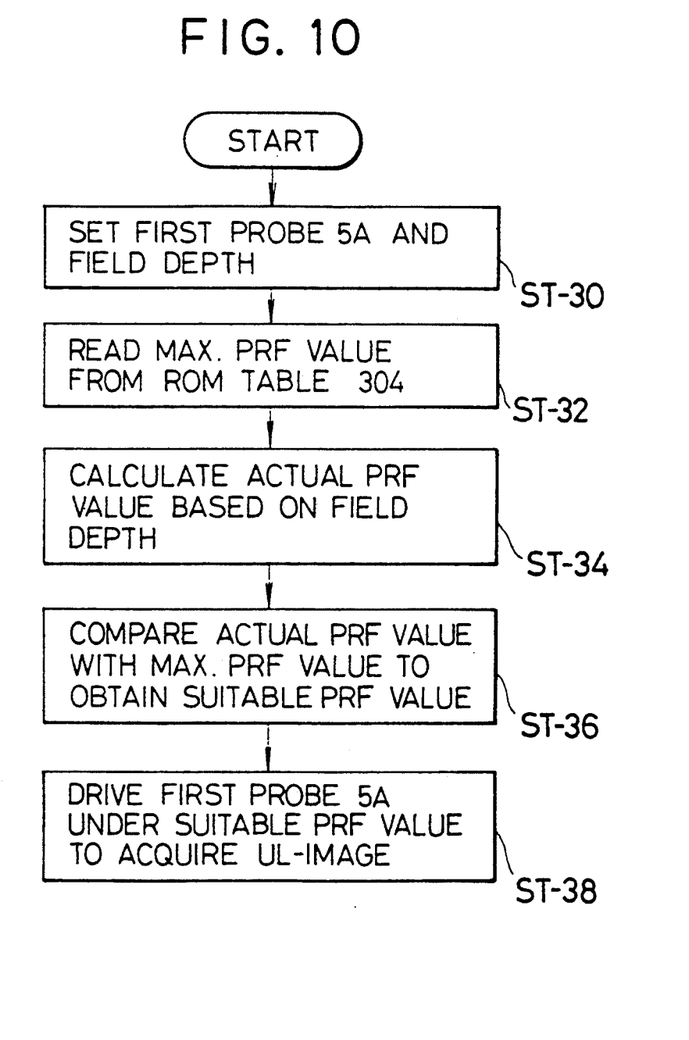
FIG. 10 is a flow chart for explaining operations of the third ultrasonic imaging system.

Referring also to a flow chart of FIG. 10, operations of the third ultrasonic imaging system will now be explained.

At a first step ST-30 of this flow chart, the following preset operations are carried out: For instance, the first ultrasonic probe 5A with the first specific transmission frequency "$f_A$ (5 MHz)" is selected, and a desired field depth (e.g., 8 cm) is set through the operation unit 62.

Then, the data about the maximum (upper limit) PRF value defined to the first transmission frequency "$f_A$" is read out from the ROM table 304 under control of the system controller 302 at a step ST-32.

Subsequently, the calculator 306 calculates an actual PRF value based upon the preset field depth in accordance with a predetermined PRF calculating formula at a step ST-34. At the next step ST-86, the comparator 308 compares the actual PRF value calculated by the calculator 306 with the maximum PRF value read out from the ROM table 304 to obtain a PRF value (e.g., 7.8 KHz) suitable for the mounted first probe 5A.

Finally, under control of the system controller 302, the first ultrasonic probe 5A with the first transmission frequency "$f_A$ (5 MHz)" is driven by the transmitter/receiver unit 3 under the suitable PRF value (7.8 KHz) and the preset field depth (8 cm) to acquire an ultrasonic image signal of the scanned interior within the biological body under medical examination. Accordingly, a desirable ultrasonic image of this scanned interior can be monitored by the TV monitor 7 with maintaining a better image quality, since this ultrasonic image signal can be acquired under no residual echoes and no idle time "IT" in the ultrasonic echoes received by the first ultrasonic probe 5A.

Thereafter, if required, the first ultrasonic probe 5A is replaced by the second ultrasonic probe 5B, and another field depth is preset via the operation unit 62 in order to acquire a desirable ultrasonic image signal under another suitable PRF value processed in the calculator 306 and the comparator 308.

What is claimed is:

1. An ultrasonic imaging system comprising:
    ultrasonic probe means for transmitting ultrasonic pulses having a specific transmission frequency to a biological body under medical examination and for receiving corresponding ultrasonic echoes reflected from an interior portion of said biological body to derive an ultrasonic image signal;
    storage means for storing at least one pulse repetition frequency signal, each one of said at least one pulse repetition frequency signal representing a periodic pulse sequence having a temporally constant, periodically repeating pulse repetition frequency term, wherein each one of said at least one pulse repetition frequency signal corresponds to a specific transmission frequency of said ultrasonic pulses transmitted from said ultrasonic probe means; and
    control means for reading said at least one pulse repetition frequency signal from said storage means when said specific transmission frequency is set, and for controlling said ultrasonic probe means in such a manner that said ultrasonic pulses having said specific transmission frequency are transmitted from said ultrasonic probe means within the temporal duration of a given pulse repetition frequency term and said corresponding ultrasonic echoes are received by said ultrasonic probe means are completely attenuated within a temporal duration of said given pulse repetition frequency term, thereby producing an ultrasonic image of said interior portion of said biological body by processing said ultrasonic image signal.

2. An ultrasonic imaging system as claimed in claim 1, wherein said storage means comprises a read-only memory with a conversion table.

3. An ultrasonic imaging system as claimed in claim 1, wherein said storage means and said control means together constitute a central processing unit.

4. An ultrasonic imaging system as claimed in claim 1, wherein said specific transmission frequency of said ultrasonic pulses transmitted from said ultrasonic probe means is in the range of 1 MHz to 10 MHz, and wherein said at least one pulse repetition frequency signal stored in said storage means has a frequency in the range of 1 KHz to 10 KHz.

5. An ultrasonic imaging system comprising:
    ultrasonic probe means for transmitting ultrasonic pulses having a specific transmission frequency to a biological body under medical examination and for receiving corresponding ultrasonic echoes reflected from an interior portion of said biological body to derive an ultrasonic image signal;
    field depth setting means for setting a field depth of an ultrasonic pulse scanning operation;
    storage means for storing at least one pulse repetition frequency signal, each one of said at least one pulse repetition frequency signal representing a periodic pulse sequence having a temporally constant, periodically repeating pulse repetition frequency term, wherein each one of said at least one pulse repetition frequency signal corresponds to both said specific transmission frequency of said ultrasonic pulses and said field depth set for said ultrasonic pulse scanning operation;
    control means for reading said at least one pulse repetition frequency signal from said storage means when said specific transmission frequency and said field depth are set, and for controlling said ultrasonic probe means in such a manner that said ultrasonic pulses having said specific transmission frequency are transmitted from said ultrasonic probe means and said corresponding ultrasonic echoes are received by said ultrasonic probe means within a time period determined by both said pulse repetition frequency signal and said field depth, thereby producing an ultrasonic image of said interior portion of said biological body by processing said ultrasonic image signal.

6. An ultrasonic imaging system as claimed in claim 5, wherein said storage means comprises a read-only memory with a conversion table.

7. An ultrasonic imaging system as claimed in claim 5, wherein said storage means and said control means together constitute a central processing unit.

8. An ultrasonic imaging system as claimed in claim 5, wherein said specific transmission frequency of said ultrasonic pulses transmitted from said ultrasonic probe means is in the range of 1 MHz to 10 MHz, wherein said at least one pulse repetition frequency signal stored in said storage means has a frequency in the range of 1 KHz to 10 KHz, and wherein said field depth is in the range of 1 cm to 10 cm.

9. An ultrasonic imaging system comprising:
    ultrasonic probe means for transmitting ultrasonic pulses having a specific transmission frequency to a biological body under medical examination and for receiving corresponding ultrasonic echoes reflected from an interior portion of said biological body to derive an ultrasonic image signal;
    field depth setting means for setting a field depth of an ultrasonic pulse scanning operation;
    storage means for storing at least one maximum pulse repetition frequency signal, each one of said at least one maximum pulse repetition frequency signal representing a periodic pulse sequence having the longest allowable temporally constant, periodically repeating pulse repetition frequency term for which ultrasonic pulses of a given transmission frequency may be transmitted from said ultrasonic probe means and corresponding ultrasonic echoes received by said ultrasonic probe means within the temporal duration of a single pulse repetition frequency term, wherein each one of said at least one maximum pulse repetition frequency signal corresponds to said specific transmission frequency of said ultrasonic pulses transmitted from said ultrasonic probe means;
    calculation means for calculating an actual pulse repetition frequency signal based upon a pulse repetition frequency signal calculation formula of which said field depth of said ultrasonic pulse scanning operation is a variable, wherein said actual pulse repetition frequency signal consists of a periodically repeating actual pulse repetition frequency term and wherein said actual pulse repetition frequency term is of shorter temporal duration than each one of said at least one maximum pulse repetition frequency term;
    comparator means for comparing said actual pulse repetition frequency signal calculated by said calculation means with said at least one maximum pulse repetition frequency signal read out from said storage means to determine a suitable pulse repetition frequency signal for said ultrasonic pulse scanning operation; and control means for controlling said ultrasonic probe means in such a manner that said ultrasonic pulses having said specific transmission frequency are transmitted from said ultrasonic pulse means and said corresponding ultrasonic echoes are received by said ultrasonic probe means within a time period determined by said suitable pulse repetition frequency signal, thereby producing an ultrasonic image of said interior portion of said biological body by processing said ultrasonic image signal.

10. An ultrasonic imaging system as claimed in claim 9, wherein said storage means comprises a read-only memory with a conversion table.

11. An ultrasonic imaging system as claimed in claim 9, wherein said storage means, said calculation means, said comparator means and said control means together constitute a central processing unit.

12. An ultrasonic imaging system as claimed in claim 9, wherein said specific transmission frequency of said ultrasonic pulses transmitted from said ultrasonic probe means is in the range of 1 MHz to 10 MHz, and wherein said at least one maximum pulse repetition frequency signal stored in said storage means has a frequency in the range of 1 KHz to 10 KHz.

* * * * *